United States Patent [19]
Acevedo

[11] 3,983,628
[45] Oct. 5, 1976

[54] DENTAL ARTICULATOR, NEW BIT REGISTRATION GUIDE, AND DIAGNOSTIC PROCEDURE ASSOCIATED WITH STEREODONT ORTHODONTIC STUDY MODEL

[76] Inventor: Raul Acevedo, Obi No. 144, Rio Piedras Heights, Rio Piedras, P.R. 00926

[22] Filed: Jan. 24, 1975

[21] Appl. No.: 543,773

[52] U.S. Cl. ............................................. 32/14 E
[51] Int. Cl.² ........................................ A61C 7/00
[58] Field of Search ....................... 32/32, 11, 40, 2

[56] References Cited
UNITED STATES PATENTS

| | | | |
|---|---|---|---|
| 1,205,437 | 11/1916 | Delabarre | 32/71 |
| 1,485,657 | 3/1924 | Williams | 32/32 |
| 2,775,036 | 12/1956 | Kesling | 32/14 B |
| 3,738,005 | 6/1973 | Cohen | 32/14 B |

Primary Examiner—Robert Peshock
Attorney, Agent, or Firm—Abraham A. Saffitz

[57] ABSTRACT

A novel articulating apparatus, a novel bite registration guide, and a new procedure for diagnosis and study are used for the mounting preparation and arrangement of my stereodont Orthodontic Study Model of U.S. Pat. No. 3,787,979, granted on Jan. 29, 1973.

In the form of my guide and my new articulator and my Orthodontic Study Model, there is reproduced very accurately the orthodontic parameters of the patient's dentition. The Orthodontist with this new articulator, bite registration guide, and my study model has a new and powerful tool which he can utilize in diagnosis and in treatment planning to shorten the treatment time and have better control of the desired tooth measurements.

The novel procedure comprises sequential stages as follows:

Stage A: The coronal assemblies of the Orthodontic Study Model are provided with the stone models of the crowns of the upper and lower teeth of the patient;

Stage B: The completed coronal assemblies of Stage A are coupled to my new bite registration guide in the Orthodontic Study Model to form a triad of upper and lower models with the bite registration guide; and, Stage C: The triad obtained in Stage B, consisting of coronal assemblies coupled to a bite registration and mounted on the Orthodontic Study Model, is now mounted in my new geared articulator. In the mounted position the triad assembly is an accurate reproduction of the orthodontic parameters of the patient's dentition and serves as a basis for charting future movements of each of the teeth in $x$, $y$ and i $z$ directions to provide reproducable and highly accurate monitoring of orthodontic treatment.

2 Claims, 16 Drawing Figures

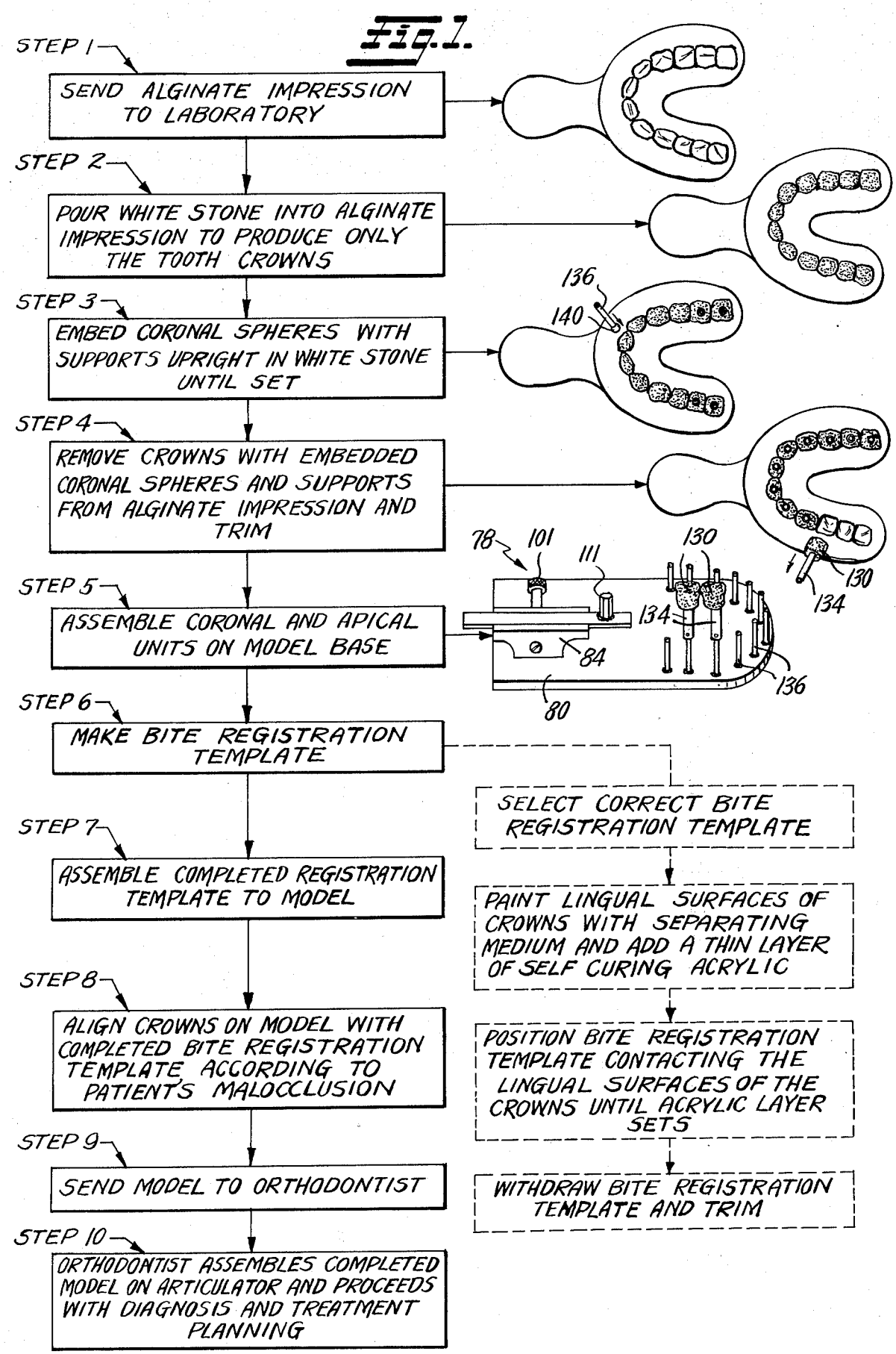

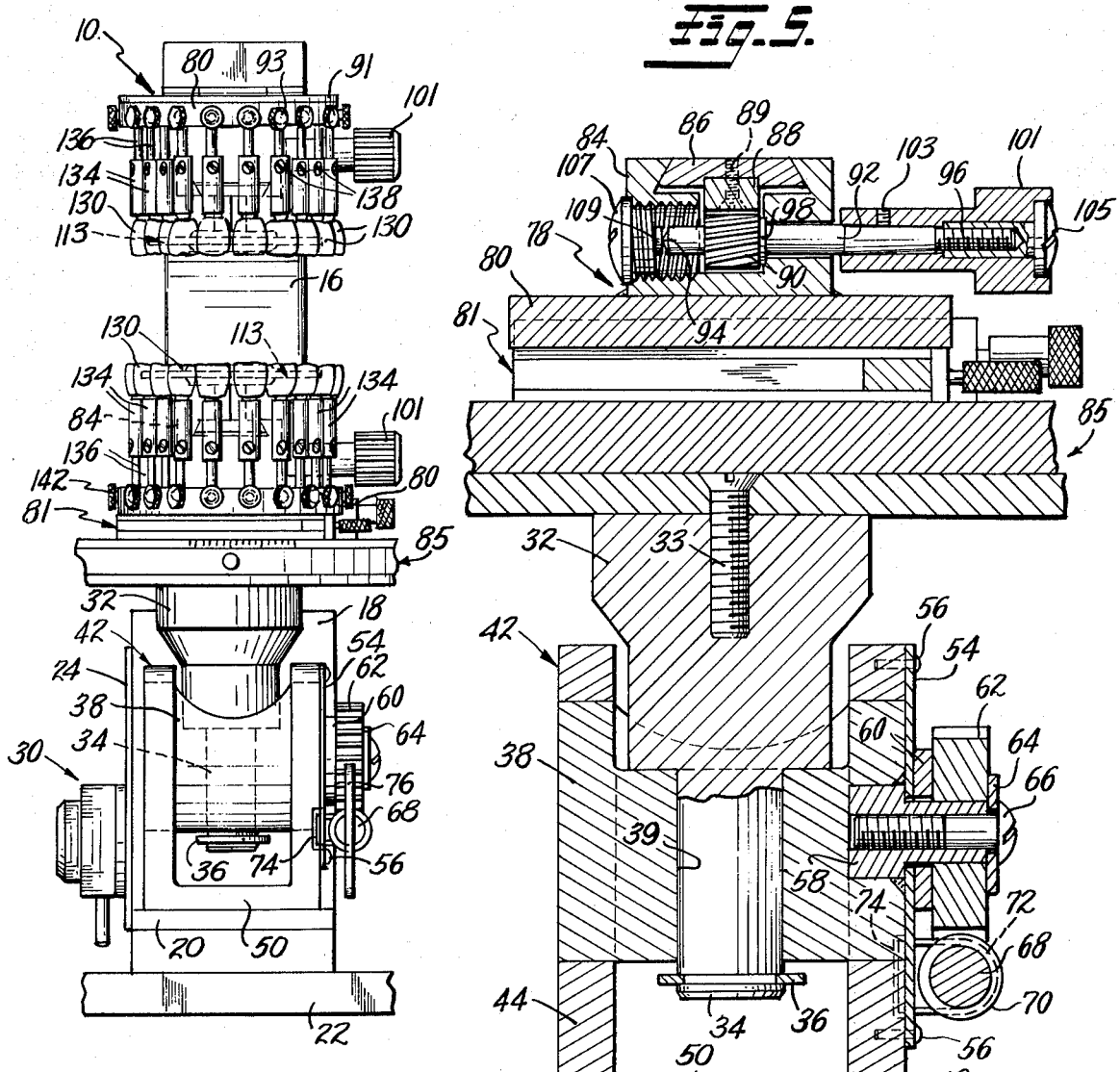
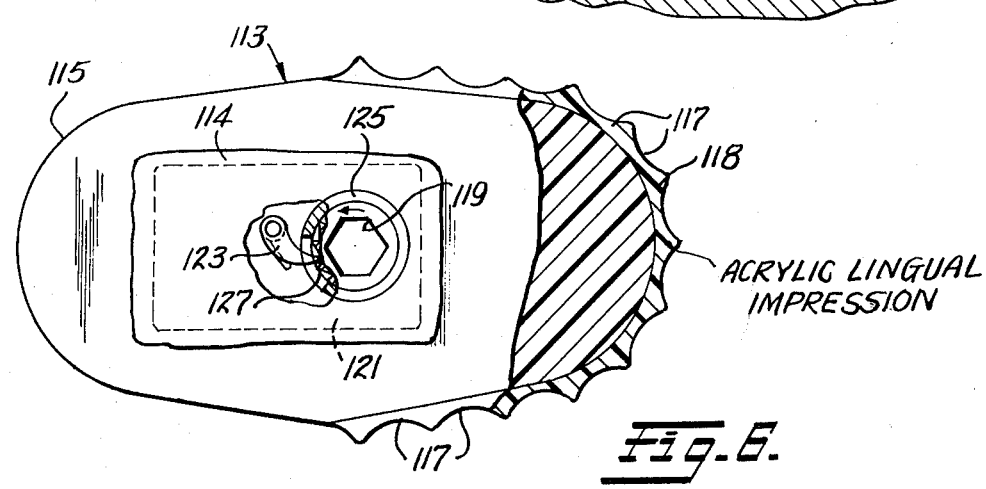

BEFORE TREATMENT

ORIGINAL CONDITION AFTER EXTRACTION OF 1ST PREMOLAR SHOWING TOOTH AXIS

CANINES UPRIGHTED

CANINES RETRACTED BY TILTING INTO EXTRACTION SPACE

ANTERIOR TEETH RETRACTED INTO SPACE

SITTING THE OCCLUSION AND CONSOLIDATION
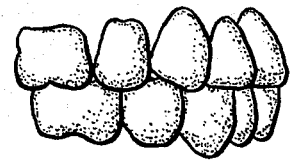
Fig. 12.
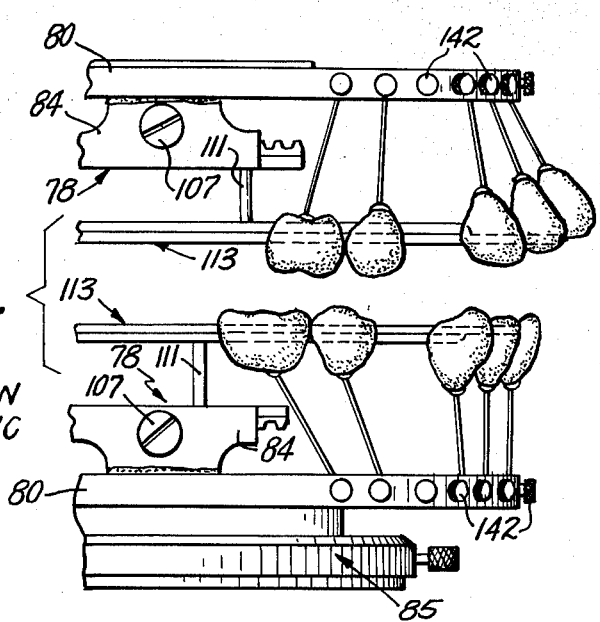
Fig. 13.
ORIGINAL CONDITION MOUNTED ON CEPHALOMETRIC STEREODENT
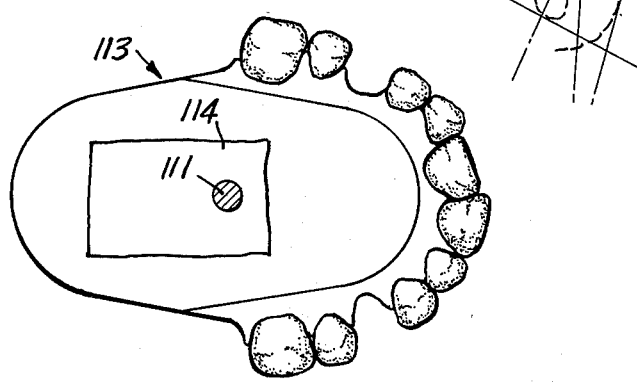
Fig. 14.
AFTER TREATMENT
Fig. 15.
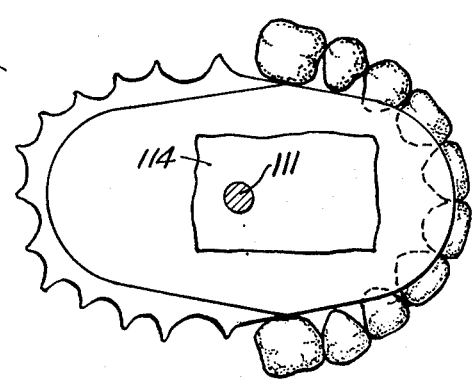
Fig. 16.

NEW DENTAL ARTICULATOR, NEW BITE REGISTRATION GUIDE, AND DIAGNOSTIC PROCEDURE ASSOCIATED WITH STEREODONT ORTHODONTIC STUDY MODEL

BACKGROUND OF THE INVENTION

1. FIELD OF THE INVENTION

This invention is in the field of Dentistry study appliances and study methods for correcting irregularities in the position and alignment of teeth in the mouth of the patient and also deals with the combination of such appliances with mounting apparatus for mounting an artificial model of the teeth simulating those of the patient in order to study the occulsion and the articulation of the model and to reproducably monitor the orthodontic treatment.

2. DESCRIPTION OF THE PRIOR ART

1. Prior Apparatus

Williams, U.S. Pat. No. 1,485,657, granted Mar. 4, 1924 discloses a dental articulator in which upper and lower model supporting members are relatively adjustable to obtain, in the practice of prosthesis, the proper position of the teeth on one model in the occlusal plane relative to the other model. Comparison may be made with the one model, the upper has been moved, after those in the other model have been arranged according to given measurements and calculations, thus the Williams device can serve for movement of the lower teeth to give measurements and calculations after the movement has been accomplished. Alternatively, the Williams device may be used to plan movement in order to reach the desired positioning of teeth in the upper and lower set.

The purpose of the Williams dental articulator is to provide certain movements and adjustments of the cooperating upper and lower tooth model parts which greatly facilitate its use in positioning these uppers and lowers before treatment is started or to monitor while it is going on or after it is finished. Because the position of the teeth in the $x$ and $y$ planes can be accurately controlled and charted with the Williams device, the use of this device will promote the accuracy of the dental work in which it is employed.

It is, however, ackward to use the Williams geared articulator with stone models based upon impressions of the teeth and a very high degree of skill is required for the Orthodontist to painstakingly chart the movements in the $x$ and $y$ plane for the present intermediate and desired tooth positions in each of the upper and lower sets.

In my U.S. Pat. No. 3,787,979, an Orthodontic Study device is provided wherein the position of each tooth may be universally adjusted. The tooth, in for form of a crown, is connected by a ball and socket joint to one end of a post which is secured at its other end to a supporting base plate. The post is in the form of elongated telescopic members whereby the height thereof may be adjusted. The post is secured to the base plate by a ball and socket joint whereby its position may be adjusted.

My Orthodontic Study device will serve to provide a precise replica of each tooth in each set, upper and lower, of the patient and will also serve to monitor positions of each tooth in intermediate and finished stages of orthodontic treatment. However, the mechanism for locating and moving the assemblies of upper and lower models in the $x$, $y$ and $z$ directions is required in order to provide the full scale utilization of my three dimensional study device in my aforesaid patent.

Wollney et al, U.S. Pat. No. 3,646,680, granted Mar. 7, 1972, presents an Orthodontic Force Model for demonstrating the direction of tooth displacement in response to externally applied forces. The Wollney apparatus is a system of springs which maintain a tooth model suspended in space. Forces are applied to this model and the direction in which the tooth is displaced as well as the amount of displacement are recorded and measured.

These forces based upon springs in Wollney can be estimated from positions in my own Orthodontic Study Model if there were available a mechanism to achieve $x$ and $y$ movements as in Williams, U.S. Pat. No. 1,485,657, but there would still be the requirement to achieve a tilting movement in the $z$ direction (vertical) absent in the Williams construction.

The panoramic tripod head of the Leitz Company, known as the Tiltall Tripod and that of Peterson, U.S. Pat. No. 2,461,175, granted Feb. 8, 1949, are swiveling mechanisms which provide the free rotations and tilting movements required for panning in photography.

If the Williams articulator in U.S. Pat. No. 1,485,657 were to be combined with my prior U.S. Pat. No. 3,787,979, one would have an adjusting mechanism for bringing the lower and upper dental arch into position in respect to the $x$, $y$ and $z$ axes, but one would not have the ability to adjust the angle of tilt required by the jaw bone structure so that one would make calculations and measurements for planning treatment and for establishing the diagnosis without having the unique tilt of the jaw structure and the positioning of the teeth relative to the jaw bone structure as the factor which will permit achieving the desired bite.

Accordingly, the requirement for a proper and true understanding of the geometry of each of the teeth goes beyond the combination of my prior study model with the aforesaid Williams patent, particularly since the jaw structure is tilted and the relationships of the teeth and the upper and lower dental arches must be defined in precise relation to the existing jaw structure, the bite, the head structure, etc., all of these determined by X-ray. The deficiencies of a simple mounting of my three-dimensional of Stereodont Model of my aforesaid patent in the Williams articulator will be overcome by utilizing a triad of my new bit registration guide and complete coronal assemblies, this triad mount in my new geared articulator is characterized by a swiveling mechanism for free tilting movement in an entirely new relationship which permits extremely accurate measurement and charting as good as or better than the most accurate micrometric measurements using an accurate measuring microscope.

PRIOR ART ORTHODONTIC PROCEDURES

The process associated with routine orthodontics consists of the following steps:

Step 1: It is routine for the Orthodontist to send to the laboratory the usual standard Alignate Impressions of the teeth of the patient. In the routine prior art practice, the laboratory pours its impression in white stone, trims, polishes, labels it and sends it back to the Orthodontist as the "Stone Model" of that patient. This is a routine procedure familiar to all who have been fitted in prosthetic dentistry.

Step 2: The stone model of the patient for the uppers and the lowers is placed in an articulator and a record is made of the position of each of the teeth.

Step 3: A dental arch representing the ideal arch for the patient's dimensions is superposed over each of the stone models in order to estimate the displacements of the teeth which require movement.

Step 4: A plan for the treatment is set forth based upon Steps 1, 2 and 3 above reflecting the condition of the patient and best judgement of the Orthodontist.

Laborious hand measurements of each of the teeth and detailed charting for planning tooth movement are essential aspects of the careful examination of the stone models and the charting procedures in Steps 2, 3 and 4 above in the prior art.

SUMMARY OF APPARATUS INVENTION: NEW APPARATUS FEATURES

Bite Registration Guide

In carrying out a basic alteration of the above conventional orthodontic procedures, my invention contemplates the creation of a bite registration guide which starts with the stone models but which adds the following steps:

a. From the stone impressions of the patient in Step 1, the laboratory pours a second stone model, but this time the model is made of the crowns of the teeth only. Thus the first model is the complete repleca while the second is a crown model.

b. While the stone is still soft and before it sets, a coronal sphere is embedded in each crown with the post held uprights until the stone sets, to provide support for the stereodont mountings. c. The individual crowns are now removed from the alginate impression and are trimmed. The laboratory man selects one Stereodont base containing the apical ball and sockets and their posts (apical assemblies) to mount these in the crown model prepared in (b) above.

d. The laboratory man inserts each coronal assembly into its corresponding apical assembly to produce the upper and lower stereodont assembly mounted on the crown model.

e. The Bite Registration Guide. A bite registration blank comprising a piece of laminar acrylic ester or vinyl chloride paste polymer plastic ⅛ inch thick having the general parabolic contour of the dental arch, but smaller in width, is provided in at least three different sizes for corresponding different sizes of dental arch encountered in practice.

f. After the proper size of bite registration blank is selected and fits loosely along the lingual aspects of the teeth in the original model of the patient's malocclusion, the blank is now converted into the guide by the following steps:

1. Paint the lingual surfaces of the teeth in the model with separating medium.
2. Pour a thin layer of self-curing acrylic (mixed monomer and polymer) on the lingual surfaces of the teeth.
3. Bring the bite block blank into alignment and contacting the poured acrylic.
4. Hold the blank in position until the acrylic sets.
5. Remove the bite registration blank and trim it. This plate how now impressed on its periphery, the lingual surfaces of the teeth as they are in the original malocclusion. This plate is called the bite registration guide and is now clamped to the post of the rack and pinion assembly of the stereodont.

The bite registration guide prepared in accordance with the above steps is provided with a mounting slot or opening in a center portion thereof and provides two aspects of a dental arch of the patient, the first aspect representing actual lingual aspects of the teeth in the original model of the patient's "malocclusion) (see for instance paragraph f above) and in another aspect the bit registration guide provides the ideal dental arch which conforms to and is related to the specific malocclusion.

Microscope Like Mounting for Geared Articulator With Hinged Portion Adapting Mounting An important feature of the invention is the mounting of the bite registration guide and the teeth which are removable teeth of the stereodont to reconstruct the original malocclusion to thereby provide a model of the upper and of the lower of the patient, the upper having its own bite registration guide for the lingual surfaces of the upper arch and the lower having the bite registration guide for the lingual surfaces of the lower to thereby provide actual and ideal arches in the guide for upper and lower in a mounting in microscope like mounting for geared articulator with hinged portion adapting mounting.

In short the microscope like mount differs from the ordinary microscope in being mounted with a hing which permits the entire mounted construction to be opened, the elongating elements of the stereodont each precisely placed, each bite registration guide being mounted through its mounting slot on a pin and the assembly of microscope mounting and enumerated components closed to produce an exact replica of the teeth in the X, Y, Z measurement space which is contributed by the articulator.

The simple mounting steps place each element for orthodontic treatment in a precise relationship for actual to ideal arch in X, Y, Z space and thereby permit, for the first time, measurements using the bite registration guide as template for monitoring planning and concluding orthodontic treatment.

Tilting Table for Adjustment to Jaw Angle

An important aspect of the invention is the tilting table which is part of the microscope like mounting because only by control of the tilt of the table on which the bite registration guide is mounted can the movement of each tooth in the direction of angular tilt corresponding to jaw angle be correlated for all of the teeth in the lower arch and for all the teeth in the upper arch. This tilting table has its most important advantage achieved in practice as a result of reversal mounting for bite registration guide.

Reversible Mounting for Bite Registration Guide

A single post mounting served for positioning the bite registration guide in relation to the separately mounted teeth of the stereodont. Reversal of the bite registration guide effects a change in the positioning of the teeth from the actual malocclusion to new positions for each of the teeth corresponding to the ideal arch; one side of the bite registration guide corresponds in form to the lingual surfaces of the malocclusion while the other side is the outer boundary of the ideal arch.

All of the foregoing steps may be carried out by the laboratory technician who can carry out the following steps with the plate which is called the bite registration guide, step a, is positioned and is now clamped to the post of the Rack and Pinion assembly of the Stereodont. Thus positioned on the stereodont, the bite-registration serves as a guide to position the movable teeth of the stereodont, thus reconstructing in the stereodont the original malocclusion.

Step b: The laboratory man positions the bite registration and arranges the teeth accordingly. This assembled and organized reproduction of the malocclusion is sent to the Orthodontist.

Step c: The Orthodontist simply attaches the received stereodont to his geared articulator and proceeds with the diagnosis and treatment planning.

SUMMARY OF PROCESS INVENTION

The process invention as illustrated in the drawings herein comprises the following steps of instruction and operation to the orthodontist or his assistant:
1. send alginate impression to laboratory;
2. pour white stone into alginate impression to produce only the tooth crowns;
3. embed coronal spheres which supports upright in white stone until set;
4. remove crowns with embedded coronal spheres and supports from alginate impression and trim;
5. assemble coronal and apical units on model base;
6. make bit registration template;
7. assemble completed registration template to model;
8. align crowns on model withcompleted bite registration template according to patient's malocclusion;
9. send model to orthodontist; and,
10. orthodontist assembles completed model on articulator and proceeds with diagnosis and treatment planning.

As shown in the drawings the assembly of the coronal and apical units on the model base bring together the Stereodont Orthondontic Study Model of my U.S. Pat. No. 3,787,979, granted on Jan. 29, 1973 into $x$, $y$ and $z$ space for very accurate positioning of each of the units in respect to the dental arch of the patient. At this stage a full jaw X-ray will serve to monitor and verify the $x$, $y$ and $z$ locations.

SUMMARY OF THE BITE REGISTRATION GUIDE OR TEMPLATE INVENTION

As the pre-assembly step for the manufacture of the bite registration template, the following additional steps under Step 6 are taken:
a. select correct bite registration template;
b. paint lingual surfaces of crowns with separating medium and add a thin layer of self curing acrylic;
c. position bite registration template contacting the lingual surfaces of the crowns until acrylic layer sets; and,
d. withdraw bite registration template and trim.

The bite registration guide comprises two arches and a central mounting bore, the mounting bore permitting one arch which is the ideal arch of the size of an idal arcuate form and the other arch being the result of the lingual positioning of the teeth in precise conformity to the model of the patient.

BRIEF DESCRIPTION OF THE DRAWINGS

The invention will now be more fully described with the aid of the accompanying drawings, in which:

FIG. 1 is a schematic illustration of the steps for assembling an orthodontic dental model;

FIG. 4 is a fragmentary end elevational view of the articulator of FIG. 2 as seen from the right thereof;

FIG. 5 is an enlarged fragmentary vertical sectional view, taken on the line 5—5 of FIG. 2; and FIG. 6 is an enlarged, plan view, partially in section showing the one-way ratchet of the bite registration template and also the crown lingual impressions thereon.

FIG. 12 is a view similar to FIGS. 8, 9, 10 and 11 of a final stage just before the residual spaces are closed and the stirring of the occlusion for optimum intercuspation is attended to, wherein the closing of the spaces is identified by the legend CONSOLIDATION;

FIG. 13 shows, in diagrammatic form, the origianl condition but after extraction, as in FIG. 8, with the teeth mounted on the cephalometric Stereodont;

FIG. 14 shows, in diagrammatic form, with legends, similar to FIG. 8, the cephalometric changes resulting from treatment (extraction, uprighting retraction, and tilting of canines, retraction and tilting of anterior teeth, setting the occulsion and consolidation);

FIG. 15 shows the original condition set up on the bite registration guide corresponding to FIG. 8; and, FIG. 16 shows the condition after treatment on the bite registration guide corresponding to FIGS. 12 and 14.

DESCRIPTION OF THE PREFERRED EMBODIMENTS

Bite Registration Guide

Figure 3:
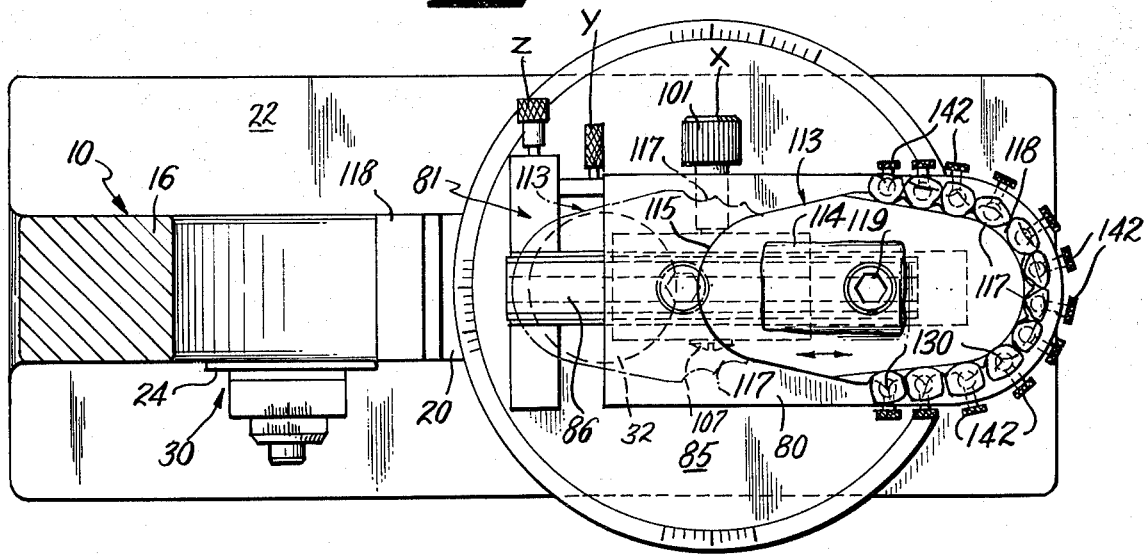
FIG. 3 is a horizontal sectional view, taken on the line 3—3 of FIG. 2.

The preferred method steps are set out in FIG. 1, starting with the taking of the impression, (step 1), pouring the stone in the tray (step 2), embedding coronal spheres with supports provided by telescoping rod means 136 and ball 140 as shown in step 3, thereafter removing the tooth crowns 130 from the alginate impression with its associated telescoping supporting means 134, to provide the assembly illustrated in step 5. The front portion of the assembly illustrated to the right at step 5 is representative of my Orthodontic Study Model in my U.S. Pat. No. 3,787,979 granted on Jan. 29, 1973, and reproduces very accurately the orthodontic parameters of the patient's dentition.

Thus, the tooth crown 130 mounted on the telescoping support means 134 and the preparation of additional stone crowns 130 provides basis for the complete upper and lower assemblies.

The bite registration template is shown in its final form in FIG. 3 in top plan view and the crowns 130 are at the forward edge, the lingual crowns 117 lying in advance of the molar crowns 130 on the right and left side respectively. The bite registration template has a rear smooth area 115 which is bounded by the arcuate perimeter constituting the idealized dimensions of the arch, these dimensions including the distance between the rear molar positions or the base, the distance between the central bore or socket 119 and the forward edge of the front surface. If one were to take the socket as the point of origin at the center focus of the parabola constituting the smooth arch of the template 113, the $y$ axis from the socket to the edge of the arcuate arch represents the base and the $x$ axis represents the height dimension of the parabola constituting the arch.

As is seen in FIG. 1, step 6, the selection of the correct bite registration template requires the measurement of the dimension between the rear molars in order to get the $x$ axis measurement and the measurement at the center line to the front teeth. The dental arches are formed of wire and are commercially available in these measurements. These wire parts constitute the smooth surface of the bite registration template 113. The preparation of the template is from a mass of self curing acrylic resin of the conventional type used and the steps for preparing this template are set out under step 6 in the blocks at the right of this step as shown in FIG. 1, these steps consisting of:

1. selecting the wire arch for the left side and the general outline of the acrylic mass;
2. painting the lingual surfaces of the crowns of the model in step 5 with a separating medium;
3. positioning the soft gel mass of self curing acrylic material into contact with the lingual surfaces of the crowns in the model;
4. permitting the acrylic mass to harden whereby the finished forward sockets of 117 (FIG. 6) as shown in top plan view in FIG. 3 are formed while the rear smooth arcuate wire bounded portion 115 forms the other side of the template, the post for the template being formed as a hexagonal post (not shown) to produce thereby a socket 119 for mounting the template.

After the bite registration template 113 has been prepared, it is checked against the positions in the Orthodontic Study Model to verify that the placement of the crowns correspond exactly to the positions that these have in the patient's mouth. To assist in this original assembling of the Orthodontic Study Model and the verification, the Orthodontic Study Model 80 itself is adapted to be mounted by mounting post 111 on to the stage of the mounting and for the purpose of positioning the Study Model on the mounting, a mounting knob 101 serves to immobilize the model 80 in a pre-set position of the track, the rear end of the base of the model 80 occupying the same relative position to the rear of the crowns on the model as the ideal arch position at the rear of the template 113 occupies in the mounting of the template shown in FIG. 3.

At this point the bite registration template is assembled and checked against the model as shown in step 7, the crowns in the model are aligned with the complete bite registration template to account for malocclusion and the bite registration model is ready for the Orthodontist's assembly which will now be described in detail in connection with FIG. 3.

As shown in FIG. 3, wheel 101 moves only the bite registration template 113 and does not move the model 80. This wheel 101 is the knob of pinion 107 shown in FIGS. 2, 3, and 5 which moves the rack and which couples the rack 88 and pinion 89 in FIG. 2 and couples rack 88, pinion 89 and slide 86 in FIG. 5.

Wheel 101 moves the bite registration forward and backward which is towards and away from the operator or that is to and from the crowns 130 of the teeth of the model. This wheel is the means for anterior and posterior movement or in the direction referred to as the $z$ axis.

Wheel 101 does not and cannot move the model 80 or the crowns 130 of the teeth with posts as shown in FIG. 1, and referred to in step 5 of FIG. 1.

Figure 2:
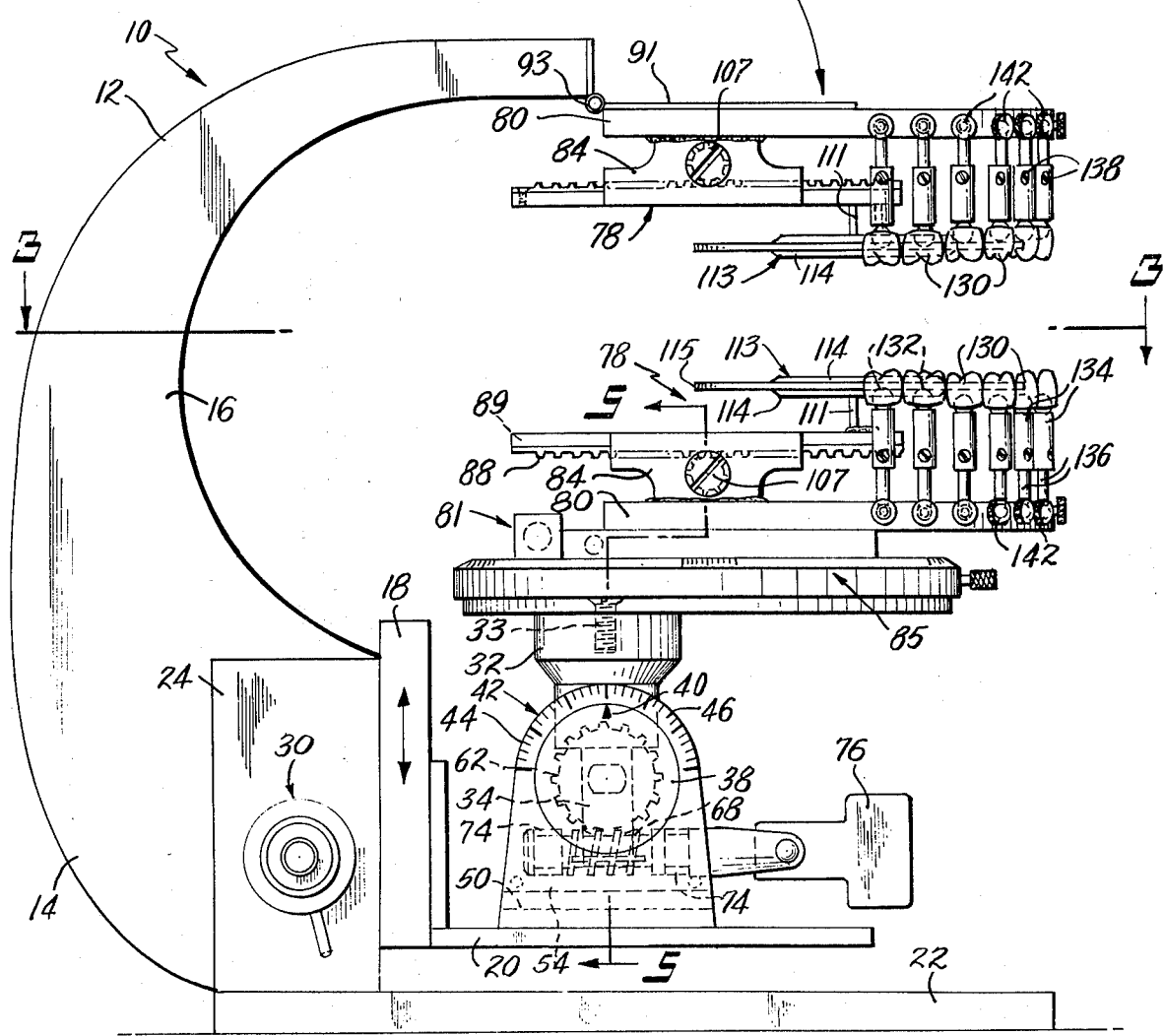
FIG. 2 is a side elevation of the articulator of the present invention showing an upper and lower orthondontic study model mounted thereon.

Wheel 101, which is the knob of pinion 107, is held within frame 84 shown in FIG. 2 and this frame 84 is rigidly attached to the base of the model 80 as is also shown in FIG. 2.

The movements brought about by wheel 101 are large movements of at least 50 mm. This is the approximate minimum distance that the anterior edge of the bite registration must be retracted away from contact with the anterior crowns so that there will be enough free space for the fingers to manipulate the crowns.

It is seen in FIG. 1 that the bite registration may be turned around to bring the opposite edge to the front, and also that once this bite registration has been used, it may be lifted up and replaced with a totally different one.

The rack and pinion mounting and adjustment was chosen instead of a simple slide because once the bite registration is brought close to the teeth, the bite registration must be held there with a high degree of rigidity while the finer movements of the crowns are being effected so as to couple or oppose each crown to its impression on the border of the bite registration. The friction provided by a good rack and pinion assembly is satisfactory for the staying power required here, while a simple slide would not be satisfactory and would lead to serious othodontic error.

The lower model 80 of the stereodont shown in FIGS. 2 – 5 can be moved in all three directions by four different wheels as follows:

a. wheel 30 provides up and down movements referred to as the y axis of base 20 in FIG. 2 and pari-passu, of everything on top of it;
b. wheel 76 provides different inclinations as required by the different Mandibular Angles;
c. the two wheels, which are marked in $x$ and $z$, are the $x$ and $z$ plane wheels which belong to the standard-stage of the microscope. In the microscope they move the glass-slide laterally on the $x$ axis and also anteriorly or posteriorly on the $z$ axis.

In this particular stage, shown in FIG. 5, knob $x$ moves the base of the model 80 in FIG. 2 along the $x$ axis which is laterally from right to left and vice-versa, while knob $z$ is for the $z$ axis or for anterior and posterior movements. The $x$-range is approximately 40 mm. while the $z$-range is approximately 60 mm. Their combined movements cover a wide expanse which is not required in the usual clinical practice of Orthodontics, but which welcomes in the research on the Comparative Anatomy and Physiology of the Dention through its evolutionary history and also as a means of framing problems for students during the teaching of the Dynamics of Occlusion; and although wide ranging, these $x$ and $z$ movements are nevertheless very fine and accurately calibrated to a fraction of a millimeter because they are used in determining the so-called "occlusal contacts," "working points," "balancing points," "overjet" and other factors in Occlusal Equilibration which is an important facet of Orthondontic Treatment. It is at this stage also that the "fine adjustment" of wheel 30 comes into play.

While the lower model has movements along the three axis, the upper model has only a hinge movement on hinge 93 in FIG. 2. This hinge provides movement over a 90° angle, from flat horizontal to straight vertical. This hinge action is equivalent to lifting the upper model away from the lower model so that:

the operator can get his hands and fingers into the space to manipulate the crowns;

the bite registration can be rotated or lifted up and out of its post 111; and, access can be had into the innerspace of the instrument for cleaning, repair and lubrication.

The bite registration and their rack and pinion assemblies for the upper and lower models are similar and are therefore almost exact mirror-images of each other.

The rotary function of 85 in FIG. 2 is also calibrated in fractions of millimeter because it participates in the study of the fine points of occlusion above described. It also establishes saggital deviations of the incisal midlines, of the buccal segments and of the mandibular condyles.

The curvature of the handle is dictated mainly by the excursion of the rack 89 as shown in FIG. 2. When this rack is in its most retracted position, the concavity of the handle must provide sufficient space for the grabbing fingers.

Summarizing the $x$, $y$ and $z$ movements, the $z$ axis movements are effected by three different wheels:

in the upper member, wheel 101, moves the upper bite registration only and not the model anteriorly and posteriorly;

in the lower member, wheel 101, moves the lower bite registration only and not the model along the $z$ axis, which is anteriorly and posteriorly;

un-numbered wheel $z$ moves the lower model along the $z$ axis.

The $y$ axis movements which are up and down: only wheel 30 does this, but it has both coarse and fine adjustments.

The $x$ axis movement which are laterally: only un-numbered wheel $x$ moves the lower model laterally.

Rotation on the horizontal plane is by stage 85 only.

Rotations on the vertical plane, which is a hinge-like movement, occurs at two places:

at simple hinge 93 for the upper model; and, at worm-gear assembly 76, 68 and 62 for the lower member.

It should be noted that the present detailed construction of the new dental articulator illustrated in FIGS. 2 – 5 and in particular the detailed showing of the gearing therein includes certain common mechanical movements with a conventional microscope, especially for the vertical movements which brings table 85 into the proper relationship to the base 80 of the model. The $x$ and $y$ movements in the present drawings are similar to the $x$ and $y$ movements of the Williams articulator in U.S. Pat. No. 1,485,657, acknowledged as the prior art herein, and details of the movements of the control knobs for the $x$ and $y$ movements for the rack and pinion are evident from the drawings herein, especially FIGS. 2 - 5.

The support 32 for the circular or rotary stage 85 is anchored by means of screw 33, and the operation of this circular or rotary stage is the same as in the circular stage of a microscope. The tilting operation for the pan head in FIG. 2 under the control of shaft 68 fitted in recesses 74 to engage gear 34 is comparable to that of a pan head used in photography, but the operation has been uniquely simplified in the present construction, which permits centering on indicating mark 40 at the middle of the scale provided by the setting at the index 46. This tilt housing 42 is a wholly new feature in the art of dental articulators.

The rack and pinion tables for the study model 80 are comparable to those in the Williams patent just mentioned. The coarse and fine vertical adjustments for the articulator are provided by adjustment means 30 and the movement of the assembly is similar to adjustments in a microscope as shown by the up and down arrow for vertical flange 18 but there are no optics. Assembly and disassembly of the tilt mechanism is facilitated by virtue of recesses which accommodates shaft 34 and recess 74 for plate 54, the bight portion of 74 fitting in the relationship shown in FIG. 2. The curved handle 21 has a portion 16 which facilitates easy back and forth movement of each of the models within any limits for comparing the crowns or elements of upper to lower. The curve at the lower portion 14 is such that the placement of the tilt mechanism and the up and down coarse and fine adjustment 24 permits compactness in construction. The hinge 93 at the top of the handle support 12 is a unique structural feature which provides a parallel relation between the upper model and lower model, and thumb screws 142 can be aligned in this parallel relationship in accordance with proper procedure.

The three major axis, the $x$ axis, the $y$ axis, and the $z$ axis in relation to the lower and upper models are shown in FIG. 3 wherein adjusting wheel 101 moves the model and bite registration guide forward and backward from the lips of the X-ray, and this is identified as the $z$ direction. The movements are large movements in comparison with the other movements in the $x$ direction. The control means for the $x$ axis (sidewise) movement of the model is wheel 79 which has been identified earlier as the wheel from the mechanical stage for $x$ and $y$ movements. This $x$ and $y$ movement is now eliminated, because the vertical or $y$ axis is controlled by the coarse and fine adjustment 30.

Wheel 79 may give adjustments as little as a tenth of a millimeter. The total displacement required will be very small, perhaps a maximum of 1 to 2 centimeters. The movement up and down ($y$ axis) by control 30 is relatively large, perhaps 10 to 15 centimeters, but nevertheless, a very fine adjustment of a tenth of a millimeter must be measured with the fine adjustment. The movement in the $z$ direction (forward and backward on the jaw) must be made to a very fine accuracy, 0.1 millimeter, and is made by wheel 101. This distance traveled by the bite registration guide and model in the $z$ direction may be from 1 to 10 centimeters but is a lesser distance than the distance traveled by adjustment 30. The numerical value of these dimensions are important in teaching the uses of the machine.

OUTLINE OF OPERATION

The details of the operating stages are now disclosed in outline form.

Stage A
Preparation of Coronal Assemblies on Model Base
Step 1 (See FIG. 1)
Step 2 (See FIG. 1)
Step 3 (See FIG. 1)
Step 4 (See FIG. 1)
Step 5 (See FIG. 1)
Step 6 (See FIG. 1)
Step 7 (See FIG. 1)

Stage B
Preparation of the Assembled Stereodont
Step 1: Making the bite registration template (FIG. 1)
  a: Selection of the bite registration Blank (See substeps under Step 6)
Step 2: Positioning the bite registration on the guide and confirming to model
  a: The upper guide consists of a simple rack 88 and pinion 89 with a hexagonal post 111 which exactly fits the center opening of the bite registration guide 113 at socket 119
  b: By means of the knob 101, the rack 185 is moved to its extreme outward position.
  c: The bite registration template 113 is now affixed to the post 111 and turned so that the edge with the impressions of the teeth is nearest to the upper coronal assembly of teeth crowns 130.
  d: By means of the knob 101 the rack is moved forward until the bite registration contacts the coronal assembly of teeth crowns 130
  e: The individual crowns are now moved into close contact with their corresponding impressions in the bite registration. This results in an arrangement of the crowns similar to that in the patient Stage C
Mounting the Assembled Stereodont on the Geared Articulator
The geared articulator is a mechanical frame to position the assembled Stereodont in the equivalent orthodontic parameters of the patients dentition. These parameters ae obtained from the cephalometric analysis of the standard headplate which the orthodontist has already studied. The parameters relate certain planes and angles of the dentition to the profile, this providing an evaluation of the esthetics of the case.

GEARED ARTICULATOR

The geared articulator consists of six elements, which are shown in FIGS. 2, 4 and 5.
Handle 10 is a C-shaped piece of plastic or metal. The lower half has a square configuration to provide a stable attachment to base 22 and for attachment of the coaxial microscope type vertical adjustment 30.
Base 22 is a rectangular flat rigid plastic or metal.
Coaxial vertical adjustment 30 is the standard coaxial mechanism with control gear 62 and adjustable stops as used in the conventional Nikon Microscope.
Tilt-table support 32 is a pan-head which is modified by incorporation of a worm-gear control 62 on shaft 68 and the housing 42 has a scale 46 graduated in degrees with index pointer 40 to provide rotation in the vertical plane. Turning the knob 76 causes the gear 62 to rotate. This rotation is transmitted directly to the stem 33 attached to the shaft of the gear 62.
Rotary Stage 85 is a standard graduated, rotary stage as used in the Nikon Microscope which provides rotation in the horizontal plane.
Linear-mechanical stages 80 and 81 (upper and lower) are each standard mechanical stages as used in the Nikon Microscope and provide linear movements in the x and y directions.
Hinge 93 serves to attach the upper assembled Stereodont and provides rotation through 90° from a straight vertical to a straight horizontal position (latter shown in FIG. 2).

Stage D
Assembly to Articulator
Step 1: Clamp lower member of the assembled Stereodont on mechanical stage 81
Step 2: Clamp the upper member of Stereodont to the hinged stage 80 below ring 91
Step 3: By turning tilt knob 76, tilt the lower assembly to the angular value of the Mandibular Plane. (A cephalometric value)
Step 4: By means of the coaxial adjustment 30 raise the lower member until it contacts the upper member
Step 5: By adjustments of the rotary stage 85 the midlines of the upper and lower assemblies are brought into alignment
Step 6: By adjustment of one or both mechanical stages 80 and 81, the upper and lower first molars are brought into their correct occlusal relation
Step 7: The instrument is now ready for the orthodontist who will analyze and explain diagnosis and treatment planning

THE BITE REGISTRATION GUIDE USED AS AN ADJUNCT WITH CEPHALOMETRIC TRACING ANALYSIS AND THE TWEED AND STEINERS PROCEDURES IN DIAGNOSIS AND PLANNING

The arch wire portion of the bite registration guide is formed to an ideal shape which represents the natural curve which the teeth of the patient will take for the most desirable movement to accomplish the objective of the orthodontic treatment.

The ideal arch in the natural curve obviously matches the span of the molars, the forward ideal arch of the incisors and canine teeth, and effectively serves as a short stiff beam spring against which the basic movements of the teeth can be measured and can be related directly to a standard Cephalometric Tracing Analysis and to the entries by the Tweed and Steiners procedures which is common practice in copyrighted orthodontic charts such as those put out by the Dental Corporation of America.

The basic movements which are carried out against the arch are the same as those with the arch appliance:
labiolingual movement;
rotation;
rootmovement in a mesiodistal direction;
depression and elevation of teeth;
buccolingual and labiolingual root movement (edgewise arch only);
space closure and opening; and
the correction of arch relation by means of intermaxillary and extra-oral traction.

It should be kept in mind that the ideal arch as an essential component of the present bite registration guide provides an additional guide to orthodontic procedures because it permits the Orthodontist to evaluate the nature of the pressures which are required to move single teeth and the nature of the forces where imbricated teeth are ligatured to the arch so that the pressure is dispersed through pressure of the teeth against each other.

The ideal arch provides another important advantage especially when the arch is mounted on the new dental articulator of the invention and is used to evaluate the depression and elevation of individual teeth. The usual twin wire arch orthodontic appliance used for depression and elevation of individual teeth requires great care, especially with incisors to exert a very gentle force at the ligature of an arch wire into the channel since the apical vessels and nerves are particularly susceptible to injury by excessive elongating forces. In this case the planning for the movement of the neighboring teeth can be part of the diagnosis planning which is suggested and indeed graphically presented because of the two sides of the bite registration guide. The imbricated teeth may require movement as a group on order to accommodate the gentle forces for the incisors. The tipping of the apices of the teeth can likewise be controlled in a new manner because of the single "split-field" representation, actual bite on one side and ideal on the other, which, together with the Cephalometric Tracing Analysis, introduces the tilt displacement in the vertical or z direction. Rotations can be duplicated with the Stereodont Orthodontic Study Model and each of the seven basic movements can be charted by the Tweed and Steiners procedures in order to create a plurality of alternate orthodontic treatment plans, these being carried out by model movements with the Stereodont Orthodontic Study Model of my U.S. Pat. No. 3,787,979.

An especially valuable advantage of the bite registration guide can be achieved with the planning mesiodistal root movement can be effected in the buccal segments either with the "round arch" or with the edgewise arch with the use of second order bends. These movements tip the teeth in the buccal segment en masse at the crowns or at the apices as the operator desires.

The importance of these plan movements is based upon the fact that all of the fixed orthodontic appliances give rise to complicated anchorage problems. The reactions from the stressed sections of the arches are applied directly to the adjoining teeth and, on account of the continuity of the dental arch, to the teeth immediately beyond. The effect of these forces of reaction have to be carefully assessed and appropriate steps taken to make sure that no unwanted tooth movements take place.

Intermaxillary and extra-oral traction are frequently used with all these appliances for the purpose of correcting arch relationships and for securing adequate anchorage in some cases. There is an extensive literature dealing with these fixed appliances. These appliances introduce such a complexity of pressures and reactions into the dental arch that it is sometimes difficult or impossible to assess exactly how much pressure is being applied to any one spot. Furthermore, root form influences the movement of the teeth mechanically and the small alterations in occlusal relation and the relation of the teeth in the same arch affects the distribution of stress from day to day. Lastly, the alveolar bone is a living tissue and it does not always react in a purely mechanical way to mechanical stresses.

When an arch type of appliance has been planned and put into position, it must be carefully watched and accurate assessments made of changes that occur and particular care taken that relative movements are not mistaken for the particular movements that are the objectives aimed at.

THE ARTICULATING APPARATUS USED AS AN ADJUNCT TO CEPHALOMETRICS AND ANTHROPOMETRICS IN DIAGNOSIS AND PLANNING

Cephalometrics comprises measurement, description and appraisal of the configuration and growth changes in the skull by ascertaining the dimensions of lines, angles, and planes between anthropometric landmarks established by physical anthropologists, and between points selected by orthodontists.

The quantification of the faciodental complex by means of roentgenographic cephalometrics is a principal concern of orthodontists.

Anthropometry furnishes the dimensions of the teeth and jaws in various stages of human development, and in different races. It supplies reliable data on changes in the jaws during growth. It shows the dentist the normal variability in all the structures that concern him, and the progression of changes under changing conditions.

Downs' cephalometric analysis in 1948 was the first and most successful contribution which made of cephalometrics a valuable semantic, diagnostic and research medium in orthodontics.

The Tweed method is based on Tweed's contention that the great majority of malocclusions are characterized by a deficiency between teeth and "basal bone," which shows itself in an abnormal forward relationship of the teeth to the bodies of the maxillary and mandibular jaws.

The Tweed evaluation as described in the *Practice of Orthodontics, Volume II, at page* 868 is actually a cephalometric evaluation of the need for extraction and is used most directly in determining the amount of space available or required for correction of malocclusion.
*Salzmann, J. B. Lippincott Company, 1966, The mandible usually is characterized by excessive irregularity of the teeth, alveolodental protrusion of incisors, and frequent impaction of third molars. The forward relationship of the dental arches and forward axial inclination of the incisor teeth are responsible in large measure for malrelation of the dental arches, crowding and imbalance of the facial profile.

When the teeth in a dental arch cannot be put into regular alignment without increasing the axial procumbency of the incisors, it becomes necessary to reduce the number of teeth to be accommodated in the arch. This procedure avoids displacing the teeth in relation to the basal bone (basal arch) of the jaws which otherwise would result in an unstable dentition followed by "relapse" when the use of orthodontic appliances, including retainers, is discontinued.

Tweed conceived the diagnostic facial triangle as a basis for diagnosis and treatment planning. The facial triangle consists of tracing the following angles on the X-ray:

1. FMA — the Frankfort Mandibular Plane Angle.
2. IMA — the Incisor Mandibular Plane Angle.
3. FMIA — the Frankfort Mandibular Incisor Angle.

The above are defined in the *Practice of Orthodontics*, Volume II, page 869.

In addition consideration is given to:

A-N-B — the A-point-Nasion-B-point Angle, and

S-N — the sella-nasion line.

The above lines are also defined in the *Practice of Orthodontics*, Volume II, page 869.

Tweed established 25° as the norm for the frankfort-mandibular plane angle (FMA), and 90° as the norm for the mandibular incisor-mandibular plane angle (IMA). By extending the line through the axial plane of the mandibular incisor to the Frankfort-horizontal plane the third angle, the Frankfort-mandibular incisor angle (FMIA) of 65°, is obtained.

After the Tweed diagnostic triangle is traced on the profile roentgenogram and a template may be used in locating the apex of the mandibular incisor tooth.

The A-N-B angle indicates the mesiodistal relation of the anterior limits of the maxillary and mandibular basal arches. The normal range is from −5° to 0°, with 65 per cent of cases examined ranging from −3° to 0°.

S-N line is used for superimposing cephalometric tracings in order to obtain the facial growth changes in patients under observation. The Bolton construction also may be used.

As a result of the Tweed procedure and based upon hundreds of studies, the angles are related to each other by means of a FMIA formula. Tweed adopted an FMA range of 16° to 35° with an average norm of 25°. If the FMA is 16° to 25° less extraction is necessary than when the FMA is upward of 30°. When FMA is 30° the mandibular incisor must be tipped to 85° to maintain 65° for the FMIA.

The A-N-B angle is reduced by the following method:
1. Distal movement of the A-point
2. Mesial movement of the B-point
3. Combination of the above.

The above very brief summary of the Tweed method illustrates recommendation for extraction and the specific use of orthodontic appliances.

It will be seen that by the Tweed method available dental arch space is recorded by measuring the mesiodistal dimensions of all teeth present or that should be present in the mouth mesial to the 1st molars on both sides. Also by the Tweed method a profile roentgenogram correction is planned and carried out.

The diagnostic facial triangle is drawn on the profile roentgenogram. A dotted line is drawn from the apex of the most forward mandibular incisor to the Frankfort horizontal at the desired FMIA of 65°. The mandibular incisor teeth will then have to be moved labially or lingually to this newly established FMIA. If 10° have to be subtracted from the existing FMIA to obtain the desired FMIA of 65° it is necessary to move the incisors inward approximately 5 mm. on each side of the mandibular dental arch.

The present articulating device correlates the precise position with both roentgenograms, the profile and the full face.

Similarly, the Steiners' procedure can be correlated to the present articulator to follow the initial placement and final placements under the treatment goal and treatment plan. The Steiner analysis compares a specific case of malocclusion to a set of norm measurements. This is used then as a basis for planning treatment in the individual patient. Variations from the norms presented depend on certain factors that occur in individual patients. Steiner's method of cephalometrics can be divided into the following three steps:

1. Diagnosis. Determine the nature of the dentofacial abnormality.
2. Treatment Goal. What can be done to correct the anomaly.
3. Treatment Plan. The treatment indicated to accomplish the treatment goal.

Under the Steiner treatment a profile analysis is made for the varying stages of treatment and a very accurate evaluation of the success of the treatment can be made in difficulty cases where the mandibular arch and its anchorage are to be changed for permanent improvement.

It is recognized that the Tweed and Steiner procedures are only a few of the large number of procedures which utilize cephalometric analysis to change the facial appearance and the dentition of the patient. For each of these, there is a need for accurately positioning nodels of the patients dentition against standard roentgenograms to add an additional quantitative dimension to orthodontics.

USE OF THE TRIAD INVENTION WITH ACCEPTED CEPHALOMETRIC ANALYSIS

The method of using the Stereodont adds to the known cephalometric analysis procedures a precise quantitative measurement in absolute units applicable to each tooth which can be visually displayed as well as manipulated by hand. These measurements are $x$, $y$ and $z$ displacements in relation to the Frankfort plane.

In the textbooks *Practice of Orthodontics*, Salzmann, J. B. Lippincott Company, 1966, Volumes I and II, there are listed 10 different procedures on cephalometric analysis and the three different procedures on tooth ratio analysis. A brief summary of Downs, Tweed and Steiner's procedures shows the typical application of the invention.

The articulator movement of special teeth anticipates extraction or movement in a particular mode, e.g., laterially, vertically, canting, or the like. Specifically utilizing the Stereodont assembly with the full complement, we can identify the location of a particular tooth in a space available for correcting malocclusion.

In the Tweed method we are dealing with the tooth and the bone and a forward relationship in respect to the ideal lingual arch. If the arch of the bite registration guide is placed over the Stereodont replica, one can simultaneously overlay the roentgenogram to determine the movement of the tooth relative to the bone, the movement of the tooth relative to the arch on the bite registration guide, and the absolute value in millimeters in the $x$, $y$ and $z$ directions together with the angle of cant or tilt. These relationships permit the identification, by diagram, of a sector of the bite registration guide in the area of specific tooth movement or extraction. The sector of the bite registration guide defines an area, the matching of the Stereodont assembly moved against the ideal arch provides a depth relationship for this same sector, and the roentgenogram provides a delimiting dimension at the bone interface with the tooth to precisely define the depth of the sector. In short, the sector area and depth can be directly measured on the articulator with the full assembly of Stereodont and bite registration guide.

Obviously, templates may be used which would be definitive of each of the three methods of cephalometrics identified herein.

Utilizing the views of the drawings in FIGS. 2 and 3, one selects a particular tooth and describes a specific area in a sector between the bordering teeth identified in the drawing. Manipulation of the tilting table by handle 76, worm 68 and gear 34 would provide a measure of the jaw angle.

The steps are as follows:
a. extraction and relocation to provide the ideal bite;
b. improvement in facial features for plastic surgery where teeth and jaw are lost and damaged by accident; and,
c. correction of malformation in a young growing child where limitations are placed upon degree of movement or correction due to growth factors.

All three procedures, Downs, Tweed and Steiner, provide a systematic recording for diagnosis and treatment planning in which an overlay over the X-ray can be diagrammed in relation to the mandibular plane, the Frankfort plane and the facial planes. By making the plane of the bite registration guide as the Frankfort plane, the Stereodont and bite registration guide will automatically be lined up and the treatment diagnosis chart may be made on a projection screen with the aligned bite registration guide, Stereodont, and profile roentgenogram.

All of the measurements may be posted on the treatment diagnosis draft.

The present method expresses the concept of adjusting the plane of the bite registration guide in the Frankfort plane relative to the roentgenogram, and measuring the displacement of any selected tooth in millimeters along the x, y and z directions and further adjusting the angle of tilt in order to properly rotate the tooth.

CLASS II, DIVISION I EXTRACTION

We will now focus on a particular tooth and define its sector depth, sector area, and bone interface, as its critical parameters. To this effect, reference is made to FIGS. 7 – 16 for disclosing the capacities of the instrument. There is selected the most typical malocclusion: Class II, Division, requiring the extraction of the four first premolars.

Figure 7:
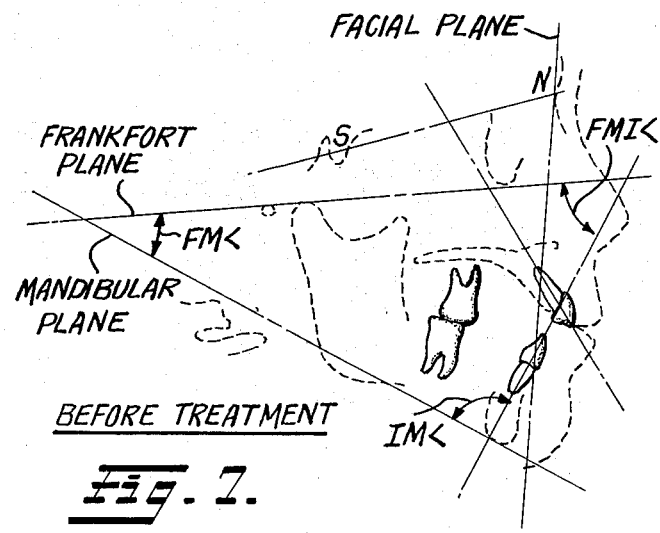
FIG. 7 is a diagrammatic view, before treatment, of a Class III, Division I malocclusion showing by legends and accepted by symbols a few of the cephalometric relations of the original condition.

FIG. 7: Shows a few of the cephalometric relations of the original condition:
1. teeth protrude considerably beyond the Facial Plane; and,
2. the molar relation is incorrect.

Figure 8:
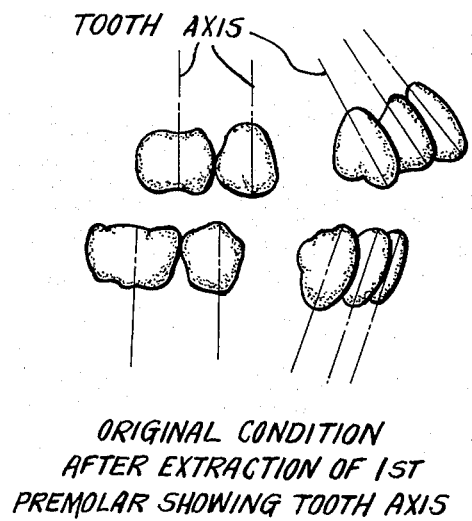
FIG. 8 is a diagrammatic view, with legends of the original condition of the teeth, after extraction of the first four premolars and showing the axis of the teeth before treatment.

FIG. 8: The teeth have been abstracted so that we may follow the treatment procedure and remedy. Note that tooth No. 4 (1st premolar) is missing due to extraction. This provides a space which is called "a deleted neighborhood."

Figure 9:
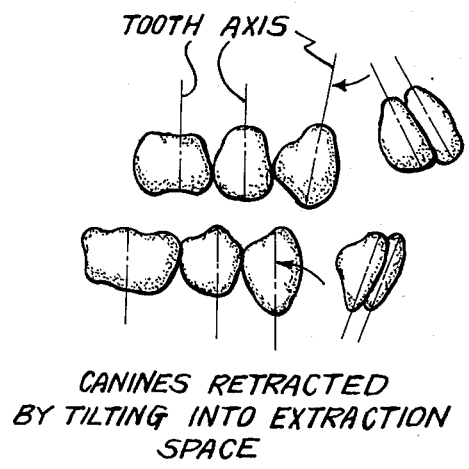
FIG. 9 is a view similar to FIG. 8 of a partial stage of treatment in which the canines are upright.

FIG. 9: The canines (No. 3) have been retracted by tilting them into the extraction space.

Figure 10:
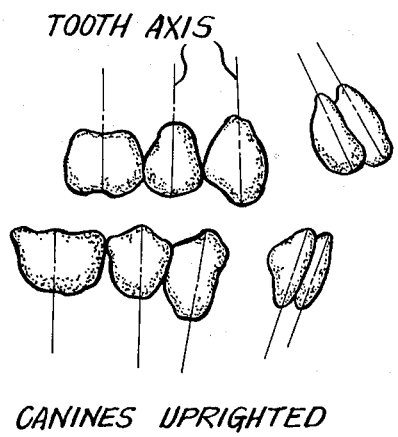
FIG. 10 is a view similar to FIGS. 8 and 9 of a later stage with legends in which the canines are retracted by tilting into the extraction space.

FIG. 10: The canines are now upright. The "deleted neighborhood" or space has now shifted to the other side (mesial) of the canines.

Figure 11:
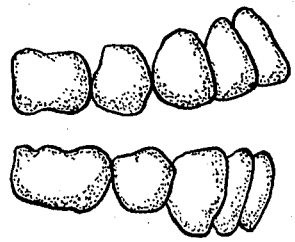
FIG. 11 is a view similar to FIGS. 8, 9 and 10 of a still later stage showing the anterior teeth retracted into the "extraction" space by means of reciprocal forces which cause a relative shift of the molars (Class II mechanics)

FIG. 11: The anterior teeth are now retracted into the space. The reciprocal forces utilized (called Class II mechanics) causes a relative shift of the molars also, which is desirable.

FIG. 12: Residual spaces are closed (consolidation) and the details of occlusion (setting the occlusion for optimum intercuspation) attended to.

FIG. 14: This shows the cephalometric changes. These are best appreciated by superposing FIG. 13 on the Frankfort plane and/or the Facial plane.

FIG. 13: Shows how the original condition is setup on the Stereodont and the full treatment procedures carried out there so as to confirm or correct the proposed Treatment Plan. The outline of the bite registration guide is shown.

What is claimed is:
1. In a method for preparing a guide for orthodontics following preparation of a stone impression of an upper and/or lower set of teeth of a patient from a colloid impression of these teeth and embedding in the colloid impression, crown models of those teeth which are to be extracted or to be moved by orthodontic procedures, that improvement consisting of preparing a bite registration guide for the malocclusion of the patient, said improved steps consisting of:
a. providing a flat mass of self curing plastic as an oval shaped body of approximately the same dimensions as the inner oval arch of the stone model of the patient, said flat plastic mass being in the soft gel condition;
b. painting the lingual surfaces of the crown models and of the stone model with a separating medium;
c. positioning the gel mass and pressing against the lingual surfaces of the crowns of the model and stone model at a medium part thereof to take an impression;
d. permitting the gel mass to harden whereby sockets corresponding to the stone model of the patient are formed in the gel mass and are hardened, the sockets representing the inner lingual surfaces of the patient's set of teeth;
e. shaping the opposite side of the mass in the form of the ideal arch for the dimensions of the stone model of the patient and affixing a wire arch at opposite sides thereto; and,
f. forming an opening in the center of the bite registration guide for mounting the bite registration guide at its center to permit rotation of the guide to show in one position the ideal arch and in the other position the actual arch of the patient.

2. The product made by the method of claim 1.

* * * * *